United States Patent [19]
Wang et al.

[11] Patent Number: 5,932,451
[45] Date of Patent: Aug. 3, 1999

[54] METHOD FOR UNBIASED MRNA AMPLIFICATION

[75] Inventors: Bruce Wang, Pacifica, Calif.; Alicia Chung, New York, N.Y.

[73] Assignee: Incyte Pharmaceuticals, Inc., Palo Alto, Calif.

[21] Appl. No.: 08/974,273

[22] Filed: Nov. 19, 1997

[51] Int. Cl.[6] .............................. C12Q 1/68; C12P 19/34
[52] U.S. Cl. ........................ 435/91.21; 435/91.2; 435/6
[58] Field of Search .............................. 435/6, 91.1, 91.2, 435/91.21, 91.51; 536/23.1, 24.1, 25.3

[56] References Cited

U.S. PATENT DOCUMENTS

| | | | |
|---|---|---|---|
| 5,021,335 | 6/1991 | Tecott et al. ................................. | 435/6 |
| 5,470,724 | 11/1995 | Ahern ..................................... | 435/91.2 |
| 5,512,462 | 4/1996 | Cheng ................................... | 435/91.2 |
| 5,514,545 | 5/1996 | Eberwine .................................... | 435/6 |
| 5,545,522 | 8/1996 | Van Gelder et al. ....................... | 435/6 |
| 5,593,863 | 1/1997 | Eberwine ............................... | 435/69.1 |
| 5,716,785 | 2/1998 | Van Gelder et al. ....................... | 435/6 |

OTHER PUBLICATIONS

Heinrichs et al J. of Immuno Methods vol. 178, pp. 241–251, 1995.

Barnard, Ross et al., "Two–Step PCR Amplification of Multiple Specific Products from cDNA Using One Specific Primer and Oligo dT," *BioTechniques* (1994) vol. 16 (2):251–252.

Eberwine, James et al., "Analysis of Gene Expression In Single Live Neurons," *Proc. Natl. Acad Sci. USA* (1992) vol. 89:3010–3014.

Eberwine, James, "Amplification of mRNA Populations Using aRNA Generated From Immobilized Oligo (dT)–T7 Primed cDNA," *BioTechniques* (1996) vol. 20:584–591.

Eberwine, James, "Complementary DNA Synthesis in Situ: Methods and Applications," *Methods in Enzymology* (1992) vol. 216:80–100.

Phillips, Jennifer et al., "Antisense RNA Amplification: A Linear Amplification Method for Analyzing the mRNA Population From Single Living Cells," *Methods: A Companion to Methods in Enzymology* (1996) vol. 10:283–288.

Rao, Venigalla et al., "A Rapid Polymerase–Chain–Reaction–Directed Sequencing Using A Thermostable DNA Polymerase From *Thermus Flavus*," *Gene* (1992) vol. 113:17–23.

Idaho Technology, "The Rapidcycler" Idaho Technology, Inc. P.O. Box 50819, Idaho Falls, ID 83405.

*Primary Examiner*—Kenneth R. Horlick
*Assistant Examiner*—Jeffrey Siew
*Attorney, Agent, or Firm*—Incyte Pharmaceuticals, Inc.

[57] ABSTRACT

Methods of enzymatically producing unbiased amounts of nucleic acid from mRNA are provided. In the subject methods, a sample of mRNA is converted to ds cDNA using a primer containing an RNA polymerase site and at least one priming site. The resultant ds cDNA is then asymmetrically amplified with captureable primer to produce captureable cDNA which is then converted to captured ds cDNA. The resultant ds cDNA may then be used in a number of different applications, such as in the preparation of amplified amounts of aRNA, in the preparation of cDNA probes, and the like.

23 Claims, 3 Drawing Sheets

METHOD FOR UNBIASED MRNA AMPLIFICATION

TECHNICAL FIELD

The technical field of this invention is the enzymatic amplification of nucleic acids.

BACKGROUND OF THE INVENTION

The characterization of cell specific gene expression finds application in a variety of disciplines, such as in the analysis of differential expression between different tissue types, different stages of cellular growth or between normal and diseased states. Fundamental to the characterization of cell specific gene expression is the detection of mRNA. However, the detection of mRNA is often complicated by one or more of the following factors: cell heterogeneity, paucity of material, or limits of low abundance mRNA detection.

One method which has been developed to address at least some of the problems associated with mRNA detection is known as antisense RNA (aRNA) amplification. In this method first strand cDNA is prepared from mRNA using an oligo dT primer that comprises a RNA polymerase promoter region 5' of the oligo dT region. The first strand cDNA is then converted to ds cDNA. Finally, the double stranded (ds) cDNA is contacted with the appropriate RNA polymerase under conditions sufficient to produce aRNA. The method can be adjusted to obtain amplification of the initial mRNA of up to $10^6$ fold. The aRNA can then be used in a variety of applications as probe, for cDNA library construction and the like, where such applications include assays for differential gene expression.

Current methods of antisense RNA amplification as described above that employ RNA intermediates are not entirely satisfactory. One potential problem with current methods of antisense RNA amplification is that amplification may be biased (bias refers to the disproportionate amplification of the individual mRNA species in a given population). Another problem is that the amplification products become successively smaller with each succeeding round of amplification. Furthermore, RNA is a labile molecule.

Accordingly, there is interest in the development of improved methods of antisense RNA amplification which do not suffer from one or more the above deficiencies experienced using current methods.

Relevant Literature

U.S. Pat. Nos. disclosing methods of antisense RNA synthesis include: 5,514,545 and 5,545,522. Antisense RNA synthesis is also discussed in Phillips & Eberwine, Methods:A Companion to Methods in Enzymology (1996) 10:283–288; Eberwine et al., Proc. Natl. Acad. Sci. USA (1992) 89: 3010–3014; Eberwine, Biotechniques (1996) 20:584–591; and Methods in Enzymology (1992) 216:80–100.

SUMMARY OF THE INVENTION

Methods of making amplified amounts of nucleic acid from mRNA are provided. In the subject methods, mRNA is first converted to ds cDNA with a first primer containing an RNA polymerase promoter and at least one priming site. The resultant ds cDNA is then enzymatically asymmetrically amplified using a second captureable primer to produce amplified amounts of anti-sense captureable cDNA. Following capture of the captureable cDNA on a solid support, the resultant captured cDNA is converted to ds cDNA which may then be used for a variety of purposes, such as in the generation of amplified amounts of aRNA, in the generation of cDNA probes and the like, which products may find use in a variety of different applications, including differential gene expression analysis.

DESCRIPTION OF THE SPECIFIC EMBODIMENTS

Figure 1A:
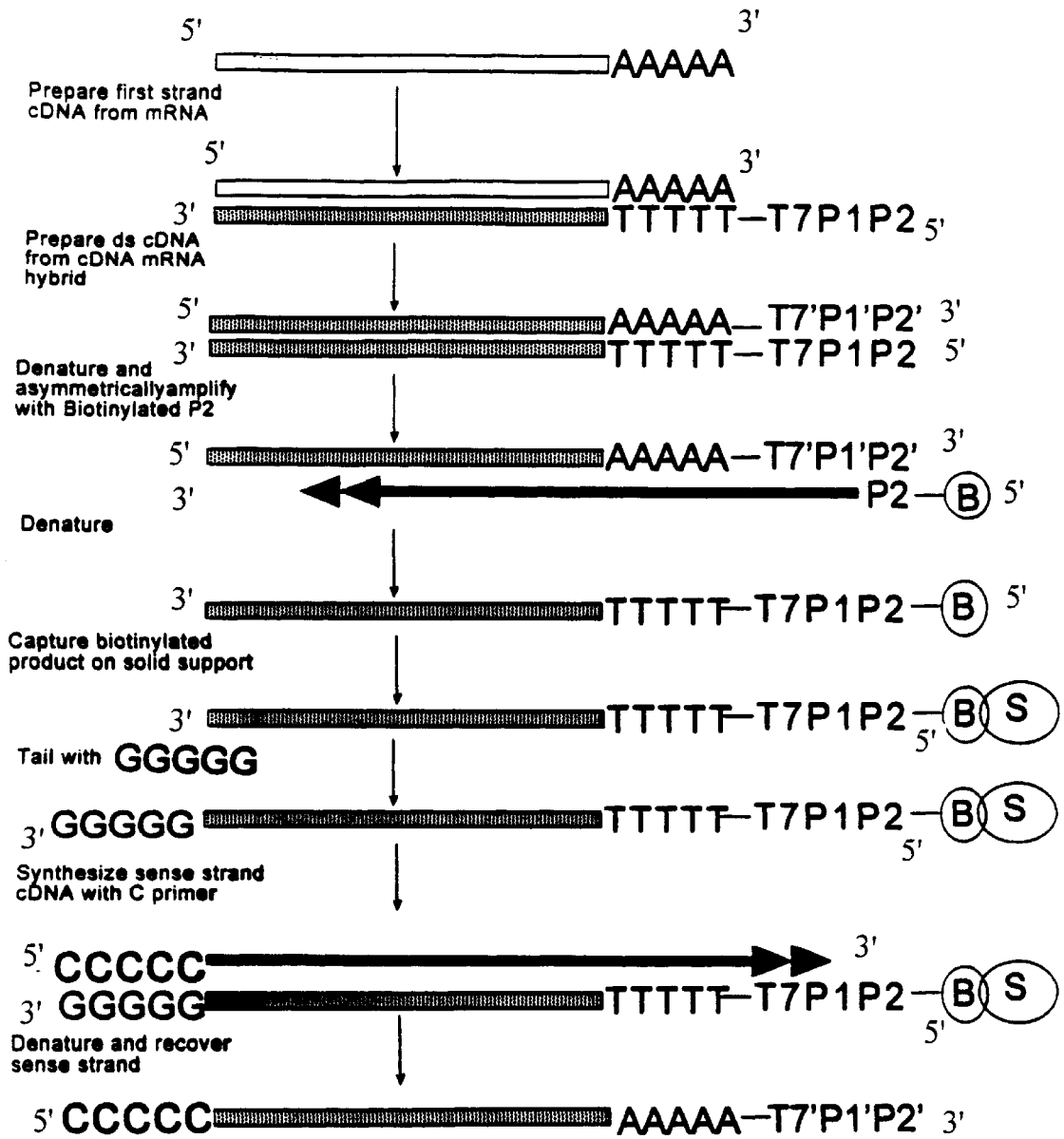
FIGS. 1A and 1B provide a schematic representation of the preparation of amplified amounts of aRNA from mRNA according to a first embodiment of the subject invention and described in greater detail in Example I, infra.

Methods of producing amplified amounts of nucleic acid from mRNA are provided. In the subject methods, mRNA is first converted to ds cDNA with a primer containing an RNA polymerase promoter and at least one priming site. The resultant ds cDNA is then asymmetrically amplified into captureable anti-sense single-stranded (ss) cDNA using a captureable primer. The resultant amplified antisense ss cDNA is then captured and converted to captured ds cDNA. The resultant ds cDNA can then be used for a variety of purposes, including the preparation of amplified amounts of aRNA, the preparation of cDNA probes and the like, where such products find use in a variety of applications, including methods for analysis of differential gene expression.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

It must be noted that as used in this specification and the appended claims, the singular forms "a" "an," and "the" include plural reference unless the context clearly dictates otherwise. Unless defined otherwise all technical and scientific terms used herein have the same meaning as commonly understood to one of ordinary skill in the art to which this invention belongs.

The subject invention provides methods for producing amplified amounts of nucleic acid from an initial amount of mRNA. By amplified amounts is meant that for each initial mRNA, multiple corresponding nucleic acids, where the term nucleic acids is used broadly to refer to RNA and DNA, are produced. By corresponding is meant that the nucleic acid shares a substantial amount of sequence identity with the mRNA, the corresponding first strand cDNA or the second strand cDNA which can be prepared therefrom, where substantial amount means at least 95%, usually at least 98% and more usually at least 99%. Generally, the number of corresponding nucleic acids produced for each initial mRNA during amplification will be at least about 10, usually at least about 50 and more usually at least about 100.

In the first step in producing amplified amounts of nucleic acids from mRNA, an initial mRNA sample is subjected to a series of enzymatic amplification reactions under conditions sufficient to ultimately produce multiple numbers of solid phase bound ds DNA for each initial mRNA in the sample that is amplified. During asymmetric amplification of the mRNA, an RNA polymerase promoter region is incorporated into the resultant product, and ultimately, the solid phase bound ds DNA that is produced therefrom.

The initial mRNA may be present in a variety of different samples, where the sample will typically be derived from a physiological source. The physiological source may be derived from a variety of eukaryotic sources, with physiological sources of interest including sources derived from single celled organisms such as yeast and multicellular organisms, including plants and animals, particularly mammals, where the physiological sources from multicellular organisms may be derived from particular organs or tissues of the multicellular organism, or from isolated cells derived therefrom. In obtaining the sample of RNAs to be analyzed from the physiological source from which it is derived, the physiological source may be subjected to a number of different processing steps, where such processing steps might include tissue homogenization, cell isolation and cytoplasmic extraction, nucleic acid extraction and the like, where such processing steps are known to the those of skill in the art. Methods of isolating RNA from cells, tissues, organs or whole organisms are known to those of skill in the art and are described in Maniatis et al., Molecular Cloning: A Laboratory Manual (Cold Spring Harbor Press)(1989). Alternatively, at least some of the initial steps of the subject method may be performed in situ, as described in U.S. Pat. No. 5,514,545, the disclosure of which is herein incorporated by reference.

Depending on the nature of the primer employed during first strand synthesis, as described in greater detail below, the subject methods can be used to produce amplified amounts of aRNA corresponding to substantially all of the mRNA present in the initial sample, or to a proportion or fraction of the total number of distinct mRNAs present in the initial sample. By substantially all of the mRNA present in the sample is meant more than 90%, usually more than 95%, where that portion not amplified is solely the result of inefficiencies of the reaction and not intentionally excluded from amplification.

In preparing amplified amounts of solid phase bound ds DNA from mRNA according to the subject invention, first strand cDNA is initially produced from the mRNA by hybridizing a particular type of primer to the mRNA under conditions sufficient for enzymatic extension of the hybridized primer to produce a cDNA/mRNA hybrid complex.

The primers employed in first strand cDNA synthesis comprise: (a) an oligo dT region for hybridization to the poly A tail of the mRNA; (b) an RNA polymerase promoter region that is 5' of the oligo dT region; and (c) a region of arbitrary sequence, at least a portion of which is 5' of the promoter region. In preferred embodiments, the primer will be a "lock-dock" primer, in which immediately 3' of the oligo dT region is either a "G," "C" or "A" such that the primer has the configuration of 3'-XTTT . . . 5', where X is either "G," "C" or "A."

The oligo dT region will be sufficiently long to provide for efficient hybridization to the polyA tail, where the region will typically range in length from 10 to 25 nucleotides in length, usually 10 to 20 nucleotides in length, and more usually from 12 to 18 nucleotides in length.

A number of RNA polymerase promoters may be used for the promoter region of the first strand cDNA primer. Suitable promoter regions will be capable of initiating transcription of operably linked DNA sequence in the presence of ribonucleotides and an RNA polymerase under suitable conditions. The promoter will be linked in an orientation to permit transcription of the DNA. A linker oligonucleotide between the promoter and the DNA may be present and, if present, will typically comprise between about 5 and 20 bases, but may be smaller or larger as desired. The promoter region will usually comprise between about 15 and 250 nucleotides, preferably between about 25 and 60 nucleotides, from a naturally occurring RNA polymerase promoter or a consensus promoter region (Alberts et al., in Molecular Biology of the Cell, 2d Ed., Garland, N.Y. (1989), which is incorporated herein by reference). In general, prokaryotic promoters are preferred over eukaryotic promoters, and phage or virus promoters most preferred. As used herein, the term "operably linked" refers to a functional linkage between the affecting sequence (typically a promoter) and the controlled sequence. The promoter regions that find use are regions where RNA polymerase binds tightly to the DNA and contain the start site and signal for RNA synthesis to begin. In E.coli, typically the RNA polymerase molecule covers about 60 nucleotides when it binds to the DNA. Native strong promoters typically contain two highly conserved DNA sequences, each about six nucleotides long, which are located upstream from the start site and separated from each other by about 17 nucleotides of unrecognized DNA. A wide variety of promoters are known. Representative promoter regions of interest include SP6, T3 and T7 as described in Chamberlin and Ryan, The Enzymes (ed P. Boyer, Academic Press, New York)(1982) pp 87–108.

The third region of arbitrary sequence in the primer that is 5' of the promoter region is chosen to introduce at least one additional priming site into the second strand cDNA, described below. The sequence may be any sequence, but will typically be chosen so as not to result in secondary structure formation, e.g. the sequence will usually not be GC rich. Where the sequence is chosen to provide for a single priming site, the length of the arbitrary sequence will range from 14 to 60, usually from about 18 to 40 and more usually from about 20 to 30 nucleotides in length. In an alternative embodiment, the arbitrary sequence can be sufficiently long to provide for two priming sites in the second strand cDNA, where the two priming sites may partially and even substantially overlap or be distinct, and optionally be separated by one or more nucleotides. Therefore, where the arbitrary region of the primer is to provide for two priming sites, the length of the arbitrary region may vary widely, but will generally not exceed 100 nt, and usually will not exceed 90 nt, and will generally be at least 40 nt, usually at least 50 nt. Where one wishes to amplify only a portion of the mRNA in the sample, one may optionally provide for a short arbitrary sequence 3' of the oligo dT region, where the short arbitrary sequence will generally be less than 5 nt in length and usually less than 2 nt in length, there the dNTP immediately adjacent to the oligo dT region will not be a dTTP and usually the sequence will comprise no dTTP. Such short 3' arbitrary sequences are described in Ling & Pardee, Science (1992) 257:967.

The oligonucleotide primers described above and throughout this specification may be prepared using any suitable method, such as, for example, the known phosphotriester and phosphodiester methods, or automated embodiments thereof. In one such automated embodiment, diethylphosphoramidites are used as starting materials and may be synthesized as described by Beaucage et al., Tetrahedron Letters 22: 1859–1962 (1981). One method for synthesizing oligonucleotides on a modified solid support is described in U.S. Pat No. 4,458,066. It is also possible to use a primer which has been isolated from a biological source (such as a restriction endonuclease digest).The primers herein are selected to be "substantially" complementary to the different strands of each specific sequence to be amplified, i.e., the primers should be sufficiently complementary to hybridize with their respective strands. Therefore, the primer sequence need not reflect the exact sequence of the template, and can, in fact, be "degenerate." Non-complementary bases or longer sequences can be interspersed into the primer, provided that the primer sequence has sufficient complementarity with the sequence of the strand to be amplified to permit hybridization and extension.

In preparing the first strand cDNA, the primer is contacted with the mRNA with a reverse transcriptase and other reagents necessary for primer extension under conditions sufficient for first strand cDNA synthesis, where additional reagent include: dNTPs; buffering agents, e.g. Tris.Cl; cationic sources, both monovalent and divalent, e.g. KCl, $MgCl_2$; RNAase inhibitor and sulfhydryl reagents, e.g. dithiothreitol; and the like. A variety of enzymes, usually DNA polymerases, possessing reverse transcriptase activity can be used for the first strand cDNA synthesis step. Examples of suitable DNA polymerases include the DNA polymerases derived from organisms selected from the group consisting of a thermophilic bacteria and archaebacteria, retroviruses, yeasts, insects, primates and rodents. Preferably, the DNA polymerase will be selected from the group consisting of Moloney murine leukemia virus (M-MLV) as described in U.S. Pat. No. 4,943,531 and M-MLV reverse transcriptase lacking RNaseH activity as described in U.S. Pat. No. 5,405,776 (the disclosures of which patents are herein incorporated by reference), human T-cell leukemia virus type I (HTLV-I), bovine leukemia virus (BLV), *Rous sarcoma* virus (RSV), human immunodeficiency virus (HIV) and *Thermus aquaticus* (Taq) or *Thermus thermophilus* (Tth) as described in U.S. Pat. No. 5,322,770, the disclosure of which is herein incorporated by reference, avian reverse transcriptase, and the like. Suitable DNA polymerases possessing reverse transcriptase activity may be isolated from an organism, obtained commercially or obtained from cells which express high levels of cloned genes encoding the polymerases by methods known to those of skill in the art, where the particular manner of obtaining the polymerase will be chosen based primarily on factors such as convenience, cost, availability and the like. Of particular interest because of their commercial availability and well characterized properties are avian reverse transcriptase and M-MLV.

The order in which the reagents are combined may be modified as desired. One protocol that may used involves the combination of all reagents except for the reverse transcriptase on ice, then adding the reverse transcriptase and mixing at around 4° C. Following mixing, the temperature of the reaction mixture is raised to 37° C., followed by incubation for a period of time sufficient for first strand cDNA primer extension product to form, usually about 1 hour.

First strand synthesis produces a mRNA/cDNA hybrid, which is then converted to ds cDNA. Conversion of the mRNA/cDNA hybrid to ds DNA can be accomplished using a number of different techniques. One technique which may be employed is the self-priming technique as described by Efstratiadis et al., Cell (1976)7: 279; Higuchi et al., Proc. Natl. Acad. Sci. (1976) 73: 3146; Maniatis et al., Cell (1976) 8:163 and Rougeon and Mach, Proc. Natl. Acad. Sci. (1976) 73:3418 in which the hybrid is denatured, e.g. by boiling or hydrolysis of the mRNA, and the first strand cDNA is allowed to form a hairpin loop and self prime the second strand cDNA. Alternatively the method introduced by Okayama and Berg, Mol. Cell Biol. (1982) 2:161 and modified by Gubler and Hoffman, Gene (1983) 25:263 may be employed, in which the hybrid is used as a template for nick translation. Alternatively, one may use terminal transferase to introduce a second primer hybridization site at the 3' termini of the first strand, as described by Rougeon et al., Nucleic Acids Res. (1975) 2: 2365 and Land et al., Nucleic Acids Res. (1981) 9:2251.

The second strand cDNA of the resultant ds cDNA will comprise not only a sequence of nucleotide residues substantially, if not completely identical, to the mRNA, with the exception of Ts substituted for Us, but also additional sequences of nucleotides at its 3' end which are present as a result of the particular primer used to synthesis first strand cDNA. These additional sequences present at the 3' end are: (a) the promoter region and (b) the region of arbitrary but known sequence which can serve as a primer site during subsequent primer extension reactions, as described in greater detail below.

Following production of ds cDNA from the initial mRNA, the ds cDNA is then asymmetrically amplified with a captureable primer under conditions sufficient to produce an amplified amount of captureable anti-sense cDNA. To enzymatically amplify the ds cDNA, the ds cDNA is first denatured and the second strand, i.e. sense strand, cDNA is used as a template for synthesis of a first captured DNA primer extension product.

For asymmetric amplification, the sense strand ss DNA is used as template in asymmetric amplification in at least one round of second primer extension product synthesis, where typically the sense strand DNA will be used in a plurality of rounds or cycles of primer extension product synthesis, where by plurality is meant at least 2, and usually at least 20, more usually at least 50 and typically at least 100 cycles. The primer extension products will be synthesized by the polymerase chain reaction in which only a single primer complementary to at least a portion of the 3' terminus of known but arbitrary sequence of the sense strand ss DNA is employed. The polymerase chain reaction (PCR), as well as devices and reagents for use in performing PCR, are described in U.S. Pat. Nos.: 4,683,202; 4,683,195; 4,800,159; 4,965,188 and 5,512,462, the disclosures of which are herein incorporated by reference. Of particular interest for performing this PCR step is the Rapidcycler sold by Idaho Technology Inc., Idaho Falls, Id.

The enzymatic extension is carried out in the presence of a DNA polymerase, dNTPs, and suitable buffering and other reagents necessary or desirable for optimal synthesis of primer extension product, as are known in the art. A variety of different polymerases are known and may be used in the synthesis of this first captureable primer extension product. Suitable polymerases include: *E. coli* DNA polymerase I (holoenzyme), Klenow fragment, T4 and T7 encoded polymerases, modified bacteriophage T7 DNA polymerase (Sequenase™), as well as thermostable DNA polymerases, such as Taq DNA polymerase and AmpliTaq™. Since thermal cycling is typically used in this portion of the method, a thermostable DNA polymerase is preferably employed for the synthesis of this second captureable primer extension product, where Taq DNA polymerase and AmpliTaq™ are representative of suitable thermostable polymerase. Buffers and other requisite reagents for performing PCR as described above are well known to those of skill in the art.

The captureable primer which is used in this first asymmetric amplification step is one that is capable of hybridizing to the arbitrary region of known sequence at the 3' end of the sense strand cDNA. By captureable primer is meant that the primer comprises a moiety which is capable of specifically binding to a second moiety which is associated with, usually covalently bound to, a solid support or substrate, where the captureable moiety will typically be a member of a specific binding pair, e.g. biotin and the like. The solid substrate or support will be one that facilitates separation of the bound from unbound agent, where suitable solid supports include magnetic beads or particles, and the like, e.g. streptavidin coated magnetic beads. Of particular interest in the subject methods are biotinylated primers which comprise at least one biotinylated nucleotide residue.

Following synthesis of the first captureable primer extension product (i.e. captureable sense strand cDNA), the primer extension product will be captured on a solid phase by contacting the reaction mixture with a solid support comprising a member of specific binding pair stably associated with its surface. The primer extension products are isolated by first capturing the primer extension products on a solid phase through the capture moiety at the 3' terminus of the primer extension product and then separating the solid phase from the remaining components of the reaction mixture. Capture of the primer extension products occurs by contacting the reaction mixture comprising the family of primer extension products with a solid phase. The solid phase has a member of a specific binding pair on its surface. The other member of the specific binding pair is bonded to the primer extension products, as described above. Contact will occur under conditions sufficient to provide for stable binding of the specific binding pair members. A variety of different solid-phases are suitable for use in the subject methods, such phases being known in the art and commercially available. Specific solid phases of interest include polystyrene pegs, sheets, beads, magnetic beads, and the like. The surfaces of such solid phases have been modified to comprise the specific binding pair member, e.g. for biotinylated primer extension products, streptavidin coated magnetic bead may be employed as the solid phase.

The captured primer extension product will then be separated from the remaining components of the reaction mixture, e.g. second strand cDNA, dNTPs, polymerase, and the like, by separating the solid support form the solution phase of the reaction mixture. For example, where the captured primer extension product is captured on magnetic beads, the reaction mixture may be placed on a magnetic base and the solution phase aspirated away. One or more subsequent washing steps are then generally performed, where a suitable washing buffer such as TE is introduced into the container comprising the remaining solid supports, the container contents are agitated, e.g. by vortexing, and the solution phase is removed, e.g. by aspiration.

The resultant captured ss primer extension DNA product, i.e. captured anti-sense cDNA, is then converted to captured ds cDNA, which captured ds cDNA can be used in a number of different applications. The ss captured cDNA can be converted to ds cDNA in a number of different ways, as described below.

In a first embodiment, the first captured ss primer extension DNA product is then modified at its 3' end to comprise an arbitrary but known sequence of nucleotides, which sequence will serve as a primer hybridization site for synthesizing a complementary DNA strand in order to produce a "sense strand ss DNA" which may be used in subsequent DNA asymmetric amplification steps, as described below. The arbitrary sequence which is introduced or added onto the 3' end will be from 10 to 200 nt in length, and usually from 10 to 20 nt in length, and will typically be a homopolymer, e.g. polyG in homopolymeric tailing. The sequence may be introduced onto the 3' end using terminal transferase (terminal deoxynucleotidyl transferase) in the presence of a divalent cation, where the particular cation employed will depend on the nature of the nucleotide to be joined to the 3' end, e.g. for purines, $Mg^{2+}$ is preferred, while for pyrimidines, $Co^{2+}$ is preferred. While less preferred because extra steps may be involved, the 3' arbitrary sequence may be introduced one nucleotide at a time, as opposed to being introduced in one step.

The captured primer extension product having the modified 3' end is then used as a template for the synthesis of "sense strand" ss DNA. To synthesize the "sense strand" ss DNA, a primer complementary to the arbitrary 3' sequence is hybridized to the sequence, and the sense strand is then synthesized under standard primer extension conditions, as described above and as are known in the art. The synthesized "sense strand" DNA will comprise the following regions: (a) a region at the 5' terminus which is complementary to the introduced 3' arbitrary but known sequence described above; (b) a region which is substantially identical, if not completely identical, to the initial mRNA (with the substitution of T for U; (c) a region which comprises the promoter region; and (d) a 3' region which serves as a primer binding site and is of known sequence.

In a second embodiment of the subject invention, instead of introducing a 3' terminal oligonucleotide onto the first captured anti-sense cDNA, as described in the first embodiment, a population of captured ds cDNA products is produced through use of random oligoprimers, where the random oligoprimers finding use in this embodiment of the subject invention will generally range in length from about 4 to 8, usually about 5 to 7, and will preferably be 6 nt in length, i.e. random hexamers.

The resultant captured sense strand DNA(s) can then be used in a variety of different applications, such as in the preparation of aRNA, in the preparation of cDNA probes and the like, using a number of different protocols depending on the ultimate nature of the desired product. For example, one may wish to further amplify the initial mRNA sample by performing one or more additional reiterations of the above process, where each reiteration will generally use a different captureable primer hybridizing to a different site at the 3' terminus of the sense strand cDNA.

One application in which the resultant captured cDNA(s) finds use is in the preparation of aRNA. In one method of preparing aRNA from the resultant captured cDNA(s), the captured cDNA is first denatured and the sense strand ss cDNA is made double stranded using an oligonucleotide capable of hybridizing to the RNA polymerase promoter region as the primer. The resultant ds DNA is then contacted with the appropriate RNA polymerase, e.g. T7 polymerase, under conditions sufficient to produce multiple copies of aRNA. See U.S. Pat. No. 5,514,545, the disclosure of which is herein incorporated by reference.

In another method of the making aRNA from the captured ds cDNA, the sense strand cDNA is first separated from the captured first primer extension product. Separation is typically accomplished by dissociating the complementary hybridized strands of the double stranded DNA complex and then separating the solution phase comprising the sense strand DNA from the solid phase bound first primer extension product. The captured ds DNA may be conveniently dissociated by raising the temperature of the reaction mixture, typically to a temperature between about 90 and 95° C. or by treatment with base. Following dissociation, the solid phase may be separated from the solution phase as described above. Typically, the separated solid phase will be discarded and the solution phase comprising the sense strand ss DNA will be retained for use as template in the following asymmetric amplification step.

The recovered sense strand ss DNA may then be used as template in another round of asymmetric amplification, as described above. As with the first round of asymmetric amplification, the primer used in this second round of asymmetric amplification will generally be a captureable primer. This second captureable primer will be complementary to a region of the 3' terminus of the sense strand ss DNA, where the region to which the second captureable primer hybridizes may be the same as or different from the region to which the first captureable primer hybridizes, as described above. The second captureable primer may comprise the same or different captureable moiety as the first captureable primer, where a biotinylated primer is exemplary of second captureable primers.

Following the above step where a plurality of cycles are performed, a plurality of second captureable primer extension products are produced for each sense strand ss cDNA. These captureable primer extension products are then separated from the remaining components of the reaction mixture, e.g. polymerase, dNTPs, buffer and the like, using the process described above for separation of the first captured primer extension product, e.g. by capturing the primer extension product on a solid phase and then separating the solid phase from the solution phase with subsequent washing steps. Following separation and washing, one is left with multiple numbers of solid phase bound or captured second primer extension product for each initial mRNA which has been amplified, where the captured second primer extension product has a sequence that is complementary to, and could hybridize with, the initial mRNA from which it was indirectly synthesized, i.e. from which it was amplified.

Finally, the ss captured second primer extension product is converted to captured double stranded DNA for subsequent transcription into aRNA. Since the captured second primer extension product comprises the known arbitrary sequence at its 3' end which is identical to the sequence introduced by the terminal transferase step in the synthesis of sense strand DNA described supra, the captured second primer extension product may be converted to double stranded primer extension product using a primer capable of hybridizing to this arbitrary sequence, e.g. a poly C where the 3' arbitrary sequence is poly G. Following hybridization of the primer to the 3' terminus of the captured second primer extension product, the primer is then enzymatically extended using the second captured primer extension product as template, conveniently by a suitable method such as that described above for the synthesis of "sense strand" DNA in which the first captured primer extension product is used as a template, resulting in captured ds DNA.

In this embodiment where one is interested in producing aRNA, the second general step in the subject methods is the transcription of the captured ds DNA into antisense RNA (aRNA), which RNA has a sequence complementary to the initial mRNA from which it is amplified. For this second step, the presence of the RNA polymerase promoter region on the newly synthesized second strand is exploited for the production of aRNA. To synthesize the aRNA, the solid phase captured ds DNA is contacted with the appropriate RNA polymerase in the presence of the four ribonucleotides, e.g. G, C, A and U, under conditions sufficient for RNA transcription, where the particular polymerase employed will be chosen based on the promoter region present in the ds DNA, e.g. T7 RNA polymerase, T3 or SP6 RNA polymerases, E.coli RNA polymerases, and the like. Suitable conditions for RNA transcription using RNA polymerases are known in the art, see e.g. the references described in the Relevant Literature section, supra. This embodiment finds amplification where one begins with a small population of mRNA, as this embodiment includes two rounds of asymmetric amplification as well as the final amplification that occurs during transcription of the aRNA.

Alternatively, the sense strand cDNA can be dissociated from the solid phase bound antisense cDNA, isolated and converted to ds cDNA for subsequent transcription into aRNA in solution, as opposed to on the solid phase.

The resultant aRNA finds use in a variety of applications. For example, the resultant aRNA can be used for cDNA library construction, mircroarrays for use in expression profiling analysis, construction of "driver" for subtractive hybridization assays, and the like. For example, the aRNA produced by the subject invention finds use in studies of gene expression in mammalian cell or cell populations. The cells may be from blood (e.g., white cells, such as T or B cells) be a cell or tissue derived from a solid organs, such as brain, spleen, bone, heart, vascular, lung, kidney, liver, pituitary, endocrine glands, lymph node, dispersed primary cells, tumor cells, or the like. The RNA amplification technology can also be applied to improve methods of detecting and isolating nucleic acid sequences that vary in abundance among different populations, such as in comparing mRNA expression among different tissues or within the same tissue according to physiologic state known as subtractive hybridization assays. In such assays wherein two nucleic acid populations, one sense and one anti-sense, are allowed to mix with one another, one population is present in molar excess ("driver") such that sequences represented in both populations form hybrids, whereas sequences present in only one population remain single-stranded. Thereafter, various well known techniques are used to separate the unhybridized molecules representing differentially expressed sequences. The aRNA may be used to construct this molar excess of driver.

One way of producing cDNA from the resultant aRNA is to prime the aRNA with random primers, as described above, e.g. hexamers, under conditions sufficient to produce primer extension product. In some embodiments of the subject invention, of particular interest is the use of the subject methods to prepare cDNA probes for hybridization to chips.

Depending on the particular intended use of the subject aRNA, the aRNA or any precursors thereof, e.g. second or first primer extension product, as may be desired, may be labeled. One way of labeling which may find use in the subject invention is isotopic labeling, in which one or more of the nucleotides is labeled with a radioactive label, such as $^{32}S$, $^{32}P$, $^{3}H$, or the like. Other labels may also be employed as are known in the art.

In many embodiments, one may wish to take steps to prevent or at least reduce the presence of background oligonucleotide contamination. Such steps could include appropriate enzymatic treatment at one or more stages in the method. For example, where one has prepared aRNA from cDNA, as described above, the resultant product could then be treated with DNAse in order to remove any remaining DNA, so as to obtain a product that is substantially all aRNA. Likewise where one has prepared cDNA from RNA, the reaction mixture can then be treated with RNAse in order to remove any contaminating RNA.

Also provided are kits for use in the subject invention, where such kits may comprise containers, each with one or more of the various reagents (typically in concentrated form) utilized in the methods, including, for example, buffers, the appropriate nucleotide triphosphates (e.g., dATP, dCTP, dGTP and dTTP; or rATP, rCTP, rGTP and UTP), reverse transcriptase, DNA polymerase, RNA polymerase, and one or more primer complexes of the present invention (e.g., appropriate length poly(T) or random primers linked to a promoter reactive with the RNA polymerase). A set of instructions will also typically be included, where the instructions may associated with a package insert and/or the packaging of the kit or the components thereof.

The following examples are offered by way of illustration and not by way of limitation.

EXPERIMENTAL

I. Preparation of Amplified Amounts of aRNA From mRNA

A. Preparation of ds cDNA

Single rat hippocampal cells are isolated using the procedure described in U.S. Pat. No. 5,514,545. Patch clamp electrodes are backfilled with a physiological saline solution (120 mM KCl, 1 mM $MgCl_2$, 0.5 mM $CaCl_2$, 10 mM Hepes, pH 7.3) containing a final concentration of 250 $\mu$M dNTPs, polyT-T7P1P2 promoter [(CCTGGGCCCTCCTGCTCCT-TAAACGACGGCCAGTGAATTGTAATACGACTCACT-ATAGGCGC$(T)_{24}$ (SEQ ID NO:01), 5 ng/$\mu$l]. 0.5 U/$\mu$l avian myeloblastosis virus reverse transcriptase (AMV RT; Seikagaku America Inc.). Electrode resistance is 3–5 M$\Omega$ when filled with this solution. Positive pressure is maintained on the electrode to avoid entry of unwanted material into the electrode. After seal rupture, the cytoplasmic contents are gently aspirated into the electrode. The contents of the electrode are then transferred to a sterile eppendorf tube containing additional dNTPs and AMV RT, at the same final concentration as described above. The buffer is the same as above, except that the pH is the optimum for AMV RT, 8.3. First-strand cDNA synthesis is completed after a 1 h incubation at 37° C. Phenol/chloroform extraction is performed twice and followed by addition of salt (5 M NaCl) and ethanol precipitation. The pellet is dissolved in 20 $\mu$l DEPC-treated water. It is heat denatured at 95° C. for 3 min, to separate the mRNA and first strand cDNA, and then quickly cooled on ice. Double-stranded cDNA is synthesized by the Gubler-Hoffman method in buffer (1 M Tris, pH 7.4, 20 mM KCL, 10 mM $MgCl_2$, 40 mM $(NH_4)_2SO_4$, 5 mM DTT) containing 250 $\mu$M dNTPs, T4 DNA polymerase (1U), and Klenow (1U) at 14° C. for 10 h. Second strand synthesis is followed by S1 nuclease (1U) treatment, which cuts the hair pin loop that is formed by self-priming during synthesis. The sample is phenol/chloroform extracted and ethanol precipitated. End repair is then accomplished with T4 DNA polymerase (1U) and Klenow (1U) in buffer (10 mM Tris, pH 7.5, 10 mM $MgCl_2$, 5 mM NaCl, 5 mM DTT) containing 250 $\mu$M dNTPs. The sample is phenol/chloroform extracted, ethanol precipitated, and resuspended in 20 $\mu$l DEPC-treated water.

B. Asymmetric Amplification with Biotinylated Primer

Asymmetric amplification is performed by single biotinylated primer PCR (Biotin-CCTGGGCCCT CCTGCTCCTT)(SEQ ID NO:02)(Biotin-111-dCTP from NEN Life Science, Boston, Mass.) in the Rapidcycler™ PCR cycler from Idaho Technology, Idaho Falls, Id., according to the manufacturers instructions using suggested reagent concentrations and volumes. Asymmetric amplification results in the production of multiple copies of first strand cDNA which are biotinylated at the 5' end.

C. Capture of the Biotinylated First Strand cDNA

80 $\mu$l of streptavidin coated magnetic beads (Dynabeads M-280) are washed with 2×80 $\mu$l binding and washing (B&W) buffer (10 mM Tris-HCl, pH 7.5, 1 mM EDTA and 2.0 M NaCl) and then resuspended in 50 $\mu$l of B&W buffer. The entire PCR reaction mixture from Step B is combined with 50 $\mu$l of the streptavidin coated magnetic beads (Dynal) and incubated at 37° C. for one hour with occasional mixing. The supernatant is removed while the magnetic beads are immobilized with a magnet. The beads are then washed twice with 2×100 $\mu$l of B&W buffer, once with 100 $\mu$l 1×TE and once with 100 $\mu$l of deionized water.

D. Homopolymeric Tailing of the Captured ss cDNA

The 3' end of the captured ss cDNA is tailed with a homopolymeric poly$(G)_{10}$ with terminal transferase based on the procedures described in Rougeon et al., Nuc. Acids Res. (1975) 2: 2365 and Land et al., Nuc. Acids Res. (1981) 9:2251.

E. Synthesis of Sense Strand cDNA

Sense Strand cDNA is then synthesized using the polyG tailed captured ss cDNA as template with a polyC primer under conditions suitable for sense strand synthesis, as described above.

F. Recovery of Sense Strand cDNA

The captured ds cDNA produced in Step E is then denatured. The sense strand cDNA is then separated from the solid phase bound ss cDNA and recovered.

G. Asymmetric Amplification

The recovered sense strand cDNA from Step F is then subjected to a second round of asymmetric amplification as described in Step B, with the exception that the primer employed is biotin-CCTGCTCCTT AAACGACGGC (SEQ ID NO:03). Asymmetric amplification results in the production of multiple copies of biotinylated first strand cDNA.

H. Production of Sense Strand cDNA

The biotinylated first strand cDNA of step G is then captured on streptavidin coated beads as described in Step C and converted to ds cDNA using polyC primer, as described in Step E. The Sense strand cDNA is then isolated and recovered according to Step F, and converted to double stranded cDNA using T7 primer (AAACGA-CGGCCAGTGAATTGTAATACGACTCACTATAGGCGC) (SEQ ID NO:04).

I. Production of aRNA

Purified ds cDNA from Step H is incubated at 37° C. for 3.5 to 4 h in buffer (40 mM Tris, pH 7.5, 7 mM $MgCl_2$, 10 mM NaCl, 2 mM spermidine, 8 mM DTT) containing RNAsin (20 U), T7 RNA polymerase (2000 U, Epicentre Technologies), 250 $\mu$M ATP, GTP and UTP, and varying concentrations of CTP and labeled CTP, where the ratio of CTP and labeled CTP will be chosen based on the intended use of the resultant aRNA product. The resultant product may be purified for further use.

Figure 1B:
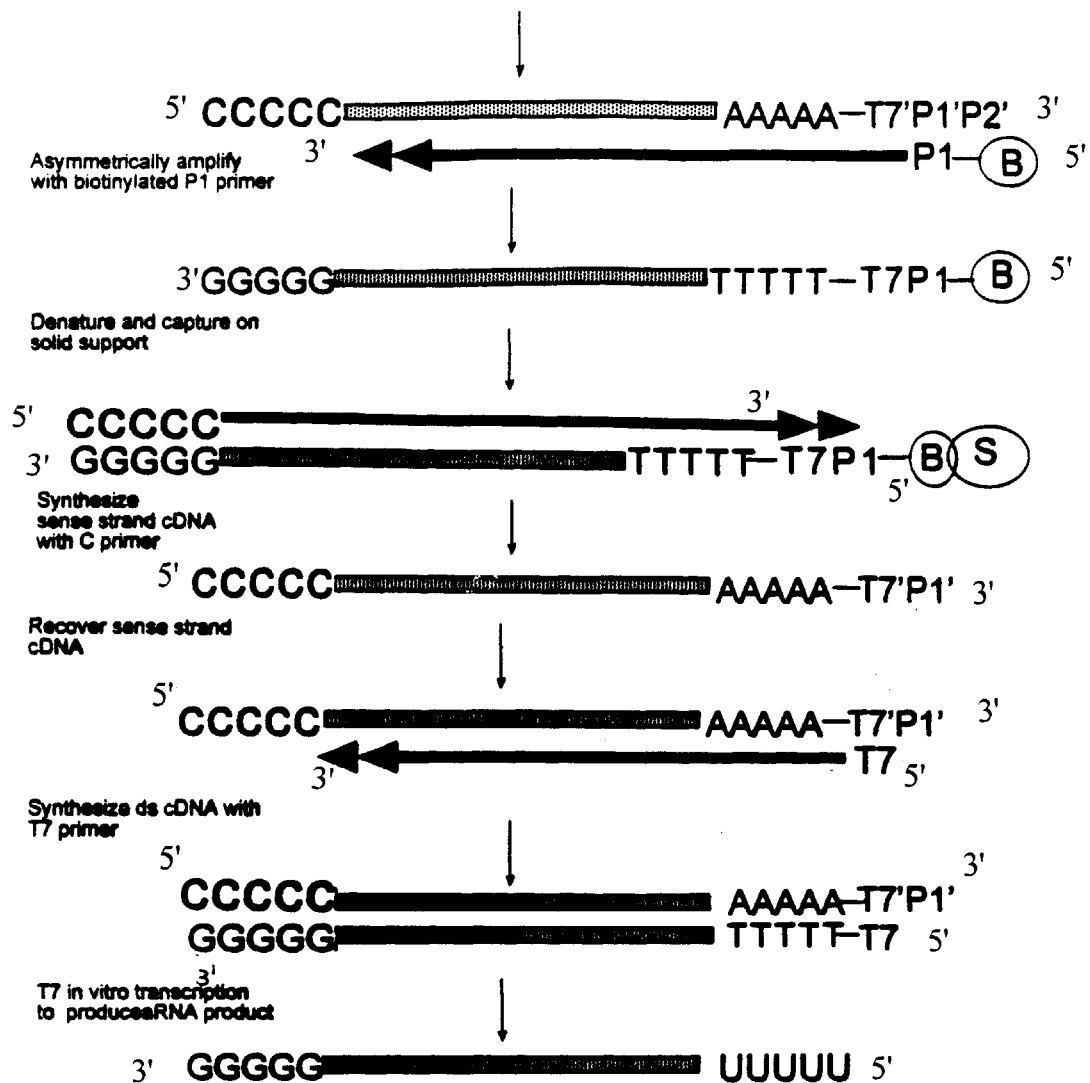

The above method is depicted schematically in FIGS. 1A and 1B.

II. Generation of Amplified Amounts of ds cDNA with Random Hexamers

Figure 2:
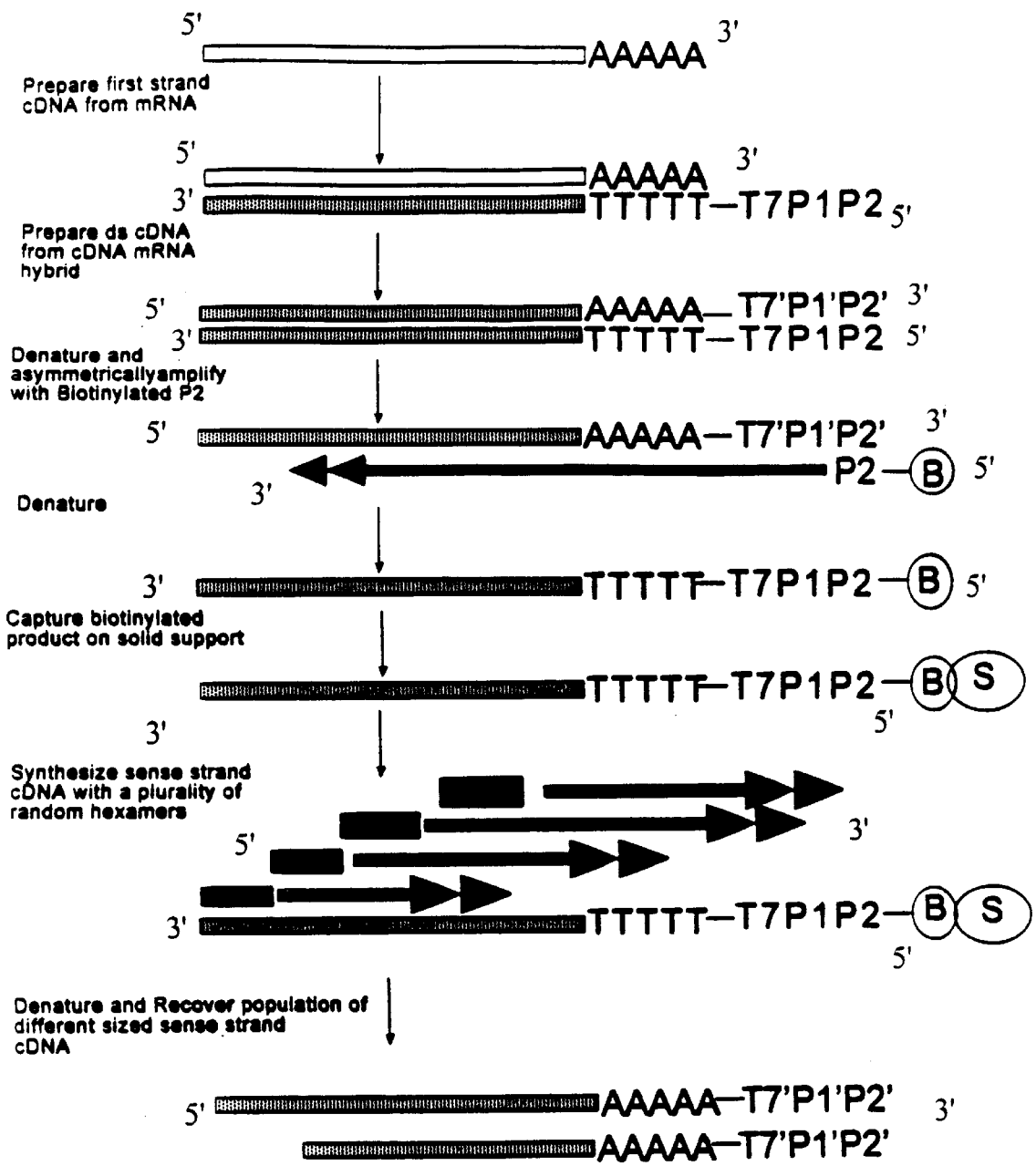
FIG. 2 provides a schematic representation of the preparation of amplified amounts of nucleic acid according to a second embodiment of the subject invention and described in greater detail in Example II, infra.

A. Steps IA–IC are performed as described above in Example I to produce amplified amounts of captured ss first strand cDNA. The resultant captured first strand cDNA is then primed with a plurality of random hexanucleotide primers under conditions suitable for sense strand synthesis, as described in 1E above, resulting in the production of a plurality of differently sized captured ds cDNAs. The resultant ds cDNAs can then be used in the production of aRNA, in the production of probes and the like. This embodiment is schematically depicted in FIG. 2.

III. Demonstration of Linear Amplification by Assymetric PCR

A 2.3 kb control RNA (Gibco BRL) was converted to ds cDNA using the Superscript Choice System cDNA synthesis kit according to the manufacturer's instructions (Gibco BRL) and a Not1 primer (5'TTCTCGAGGCTAGCGAGCTCGCGGCCGC(T)18VN) (SEQ ID NO: 05).The full length ds cDNA was gel purified over a 0.8% agarose gel with Geneclean glass beads (BIO101) and the concentration of purified DNA was determined by absorbance at 260 nm. The template as serially diluted to 55, 27.5 and 13.75 ng/μl and 6 asymmetric PCR reactions for each template concentration were set up: 1×Amplitaq PCR buffer (Perkin Elmer), 100 μg/ml BSA, 5 pmol Not2 primer (5'CTCGAGGCTAGCGAGCTC)(SEQ ID NO:06), 200 μM dATP, 200 μM dCTP, 200 μM dTTP, 200 μdGTP, 2.5 μCi $^{32}$P-dCTP (3000 Ci/mmol), 1 unit Amplitaq DNA polymerase (Perkin Elmer). Reactions were transferred to glass capillaries and were cycled in a Rapid-cycler PCR machine (Idaho Technology) at 94 for 0 sec, 58 for 3 sec, and 72 for 20 sec. the appropriate capillaries were removed at t=0, 25, 50, 75, 100 and 125 cycles. The amount of product synthesized was determined by adsorbing an aliquot from each reaction to DE-81 filters and washing with synthesized $Na_2HPO_4$. A "no DNA" control prepared as above in parallel gave a calculated 5.6 ng for 125 cycles.

| Cycle # | Starting Template | | |
|---|---|---|---|
| | 55 ng | 27.5 ng | 13.75 ng |
| | Product Made (ng) | | |
| 25 | 114 | 69 | 23 |
| 50 | 448 | 427 | 374 |
| 75 | 925 | 810 | 642 |
| 100 | 1147 | 554 | 713 |
| 125 | 1194 | 1016 | 939 |

The above results and discussion demonstrate that a novel and improved methods of producing amplified amounts of nucleic acid from an initial mRNA are provided. Because the amplification is carried out through DNA intermediates, a number of advantages are realized with the subject methods, such as the production of unbiased amounts of amplified nucleic acids, e.g. aRNA, equalized transcript size, avoidance of continued reduction in transcript size for each round of amplification, and the like.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method for producing amplified amounts of nucleic acids from mRNA, said method comprising:
    (a) converting mRNA to ds cDNA with a first primer comprising an RNA polymerase promoter region and at least one priming site;
    (b) asymmetrically amplifying said ds cDNA with a second captureable primer to produce an amplified amount of captureable antisense cDNA;
    (c) capturing said captureable antisense cDNA; and
    (d) converting said captured antisense cDNA to captured ds DNA.

2. The method according to claim 1, wherein said asymmetric amplification step (b) comprises a plurality of cycles.

3. The method according to claim 1, wherein said first primer comprises:
    (i) an oligo dT region;
    (ii) an RNA polymerase promoter region 5' of the oligo dT region; and
    (iii) at least one priming site 5' of the RNA polymerase promoter region.

4. The method according to claim 1, wherein said converting of said captured antisense cDNA to ds cDNA of step (d) comprises:
    homopolymeric tailing of the 3' terminus of said captured antisense cDNA; and
    hybridization of a complementary homopolymeric primer to said homopolymeric tail; and
    enzymatic primer extension of said hybridized primer.

5. The method according to claim 1, wherein said converting of said captured antisense cDNA to ds cDNA of step (d) comprises:
    hybridizing random oligomer primers to said captured antisense cDNA; and
    enzymatically extending said hybridized primers.

6. The method according to claim 5, wherein said method further comprises transcribing said captured ds cDNA to aRNA.

7. A method for producing amplified amounts of nucleic acids from mRNA, said method comprising:
    (a) converting mRNA to ds cDNA with a first primer comprising an RNA polymerase promoter region and at least one priming site;
    (b) asymmetrically amplifying said ds cDNA with a second captureable primer to produce an amplified amount of captureable antisense cDNA;
    (c) capturing said captureable antisense cDNA; and
    (d) converting said captureable antisense cDNA to captured ds DNA by hybridizing random oligomer primers to said captured antisense cDNA and enzymatically extending said primers.

8. The method according to claim 7, wherein said oligo dT primer comprises a T7 promoter region.

9. The method according to claim 7, wherein priming site is from 14 to 60 nt in length.

10. The method according to claim 7, wherein said captureable primer is biotinylated.

11. The method according to claim 10, wherein said method further comprises transcribing said captured ds cDNA to aRNA.

12. A kit for use in the preparation of amplified amounts of nucleic acids from mRNA, said kit comprising:

a first primer comprising in the 3' to 5' direction an oligo dT region, an RNA polymerase promoter site and at least one priming site; and a second captureable primer.

13. The kit according to claim 12, wherein said first primer comprises at least two priming sites.

14. The kit according to claim 12, wherein said first primer comprises an A, G or C at its 3' terminus.

15. The kit according to claim 12, wherein said captureable primer comprises a member of a specific binding pair bonded to its 5' terminus.

16. The kit according to claim 15, wherein said member of a specific binding pair is biotin.

17. The kit according to claim 12, wherein said kit further comprises a thermostable polymerase.

18. The kit according to claim 12, wherein said kit further comprises an RNA polymerase.

19. The method according to claim 1, wherein said method further comprises denaturing said captured ds DNA and recovering the sense cDNA.

20. The method according to claim 19, wherein said method further comprises amplifying assymetrically said recovered sense cDNA.

21. The method according to claim 5, wherein said method further comprises denaturing said captured ds DNA and recovering the sense cDNA.

22. The method according to claim 21, wherein said method further comprises amplifying assymetrically said recovered sense cDNA.

23. The kit according to claim 12, wherein said kit further comprises random oligomer primers.

* * * * *